(12) United States Patent
Breitenbach et al.

(10) Patent No.: US 6,281,282 B1
(45) Date of Patent: Aug. 28, 2001

(54) POLYMER POWDERS REDISPERSIBLE IN AQUEOUS SOLUTION

(75) Inventors: Jörg Breitenbach, Mannheim; Karl Kolter, Limburgerhof; Angelika Schmitt, Worms, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/171,826

(22) PCT Filed: Apr. 24, 1997

(86) PCT No.: PCT/EP97/02097

§ 371 Date: Oct. 27, 1998

§ 102(e) Date: Oct. 27, 1998

(87) PCT Pub. No.: WO97/42255

PCT Pub. Date: Nov. 13, 1997

(30) Foreign Application Priority Data

May 3, 1996 (DE) .............................................. 196 17 716

(51) Int. Cl.[7] ................................................. C08L 31/00
(52) U.S. Cl. ............................................ 524/556; 528/489
(58) Field of Search ........................... 523/332; 524/559; 528/489

(56) References Cited

U.S. PATENT DOCUMENTS

| Re. 28,780 | * | 4/1976 | Bergmeister | 260/856 |
|---|---|---|---|---|
| 3,653,499 | * | 4/1972 | Richter | 206/47 |
| 4,112,215 | | 9/1978 | Boessler et al. | |
| 4,520,172 | | 5/1985 | Lehmann et al. | |
| 4,539,294 | * | 9/1985 | Metcalfe | 435/180 |
| 4,542,184 | | 9/1985 | Eck et al. | |
| 4,794,167 | | 12/1988 | Lindner et al. | |
| 4,816,558 | * | 3/1989 | Rauch | 528/501 |
| 4,855,402 | * | 8/1989 | Salazar | 528/487 |
| 5,028,413 | * | 7/1991 | Bianchi | 424/52 |
| 5,093,082 | * | 3/1992 | Watanabe | 422/56 |
| 5,252,704 | | 10/1993 | Bright et al. | |
| 5,326,586 | | 7/1994 | Grabowski et al. | |
| 5,405,621 | * | 4/1995 | Sipos | 424/490 |
| 5,415,872 | * | 5/1995 | Sipos | 424/490 |
| 5,519,084 | | 5/1996 | Pak-Harvey et al. | |
| 5,576,378 | * | 11/1996 | Kuhlmann | 524/523 |
| 5,703,156 | * | 12/1997 | Sauer | 524/802 |
| 5,753,733 | * | 5/1998 | Eck | 524/265 |
| 5,874,524 | * | 2/1999 | Pakusch | 528/482 |
| 5,922,789 | * | 7/1999 | Kohlhammer | 524/17 |
| 5,962,554 | * | 10/1999 | Pakusch | 523/342 |
| 6,133,345 | * | 10/2000 | Pakusch | 523/342 |

FOREIGN PATENT DOCUMENTS

| 25 12 238 | 1/1977 | (DE) . |
|---|---|---|
| 36 16 020 | 11/1990 | (DE) . |
| 43 25 158 | 2/1995 | (DE) . |
| 88 951 | 9/1983 | (EP) . |
| 134 451 | 3/1985 | (EP) . |
| 274 053 | 7/1988 | (EP) . |
| 536 595 | 4/1993 | (EP) . |
| 601 518 | 6/1994 | (EP) . |
| 605 933 | 7/1994 | (EP) . |
| 161 326 | 11/1985 | (WO) . |
| 93/13048 | 8/1993 | (WO) . |
| 95/03790 | 2/1995 | (WO) . |

OTHER PUBLICATIONS

Derwent Abst. JP 3109409.
Phar. Acta Helv. 62, 69–88, 1986, I.L. Ford.
Physical and Chem. Data J–191–J205—Handbook of Biochemistry Sober, Chemical Rubber Co.
K. Thom et al., Pharm. Ind. 51, 98–101 (1989).
Buffer Solutions, Physical and Chemical Data J–195–J–199.

* cited by examiner

*Primary Examiner*—Paul R. Michl
(74) *Attorney, Agent, or Firm*—Keil & Weinkauf

(57) ABSTRACT

Polymer powders redispersible in aqueous solution, their use in cosmetic, pharmaceutical or crop protection formulations and a process for preparing polymer powders redispersible in aqueous solution comprising copolymers carrying free acid or base groups and, if appropriate, auxiliaries, which comprises adjusting the pH of the dispersion prior to drying by the addition of at least one buffer system to a pH of from 2.0 to 6.5 in the case of copolymers carrying free acid groups or a pH of from pH 7.5 to 12 in the case of copolymers carrying free base groups.

6 Claims, No Drawings

POLYMER POWDERS REDISPERSIBLE IN AQUEOUS SOLUTION

DESCRIPTION

The present invention relates to a process for preparing polymer powders redispersible in aqueous solution comprising copolymers carrying free acid or base groups and, if appropriate, auxiliaries, which comprises adjusting the pH of the dispersion by the addition of a buffer system to a pH of from 2.0 to 6.5 in the case of copolymers carrying acid groups or a pH of from 7.5 to 12 in the case of copolymers carrying base groups.

The invention further relates to polymer powders redispersible in aqueous solution and their use in cosmetic and pharmaceutical formulations and compositions for crop protection.

Patent DE 2 512 238 discloses film-forming polymer powders prepared from aqueous plastic dispersions. These film-forming powders are used, after dissolution in an organic solvent, for coating solid drug formulations.

The use of organic solvents when coating solid drug formulations presents considerable technical problems. All the equipment used has to be explosion-proof to prevent ignition of the solvent. For environmental and cost reasons, the evaporated solvent has to be recovered from the waste air. In addition, the solvent has to be removed completely from the pharmaceutical formulations. Alternatives to using organic solvents were therefore sought.

Consequently, a number of processes employing water as solvent were developed. However, these processes have a number of disadvantages.

In U.S. Pat. No. 5,252,704, Bright et al. disclose redispersible polymer powders which can be prepared from copolymers by adding large amounts of polyvinylpyrrolidone prior to spray-drying. The high percentage of polyvinylpyrrolidone added, however, detrimentally affects the solubility of the polymer film obtained after film-forming.

EP-B 88 951 and EP-B 161 326 disclose the redispersion of emulsion polymer powder having free carboxyl or amino groups by converting these groups into their salts. Free carboxyl groups are thus converted into their salts by adding bases, and free amino groups are converted into their salts by adding acids. This is carried out after drying the polymer dispersion, by stirring an alkaline solution into the carboxyl-containing polymer powder which is finely dispersed in water.

If the polymer carries free amino groups, an acid solution is stirred in for dispersion.

For carboxyl-containing polymers, the possibility of partial neutralization of the free carboxyl groups by adding alkali prior to spray-drying has been described.

In this case, however, the dispersion viscosity and the degree of coagulum formation prior to spray-drying are critical parameters. In addition, if the alkali is added prior to drying, undesirable coagulum is easily formed during the subsequent redispersion. The neutralization of the polymer powders, ie. the salt formation, is therefore preferably carried out after drying the powders, just before the solid drug formulations are prepared. For the user, this poses the problem of having to provide additional facilities for the neutralization and storage of the bases or acids.

It is an object of the present invention to develop redispersible polymers which can be dispersed directly without the disadvantages described to give an aqueous solution, and to make them available for applications in the cosmetic and pharmaceutical sectors and in crop protection.

We have found that this object is achieved by adjusting the pH of the dispersion prior to drying by the addition of at least one buffer system to a pH of from 2.0 to 6.5 in the case of copolymers carrying acid groups or a pH of from 7.5 to 12 in the case of copolymers carrying base groups, so as to provide a polymer powder which is readily redispersible.

The polymer powder according to the invention, which has a very long shelf life, redisperses quickly in aqueous solution without forming coagulum, for example.

They are [sic] therefore ideally suitable as a film former in cosmetic, pharmaceutical or crop protection formulations.

Suitable buffers for the process according to the invention are, in principle, all known buffers such as described for example in Handbook of Biochemistry (H. A. Sober, R. A. Horte (Eds.). The Chemical Rubber Co., J 195-J 199, 1968).

The pH of the dispersion containing copolymers carrying free acid or base groups is advantageously adjusted prior to drying by the addition of at least one buffer system to a pH of from 2.0 to 6.5 in the case of copolymers carrying acid groups or a pH of from 7.5 to 12 in the case of copolymers carrying base groups. Preferably, the pH is adjusted prior to drying to a pH of from 3.0 to 6.0 in the case of copolymers carrying acid groups and to a pH of from 7.5 to 11 in the case of copolymers carrying base groups. By adjusting the pH, some of the free acid or base groups of the copolymers are converted to their salts.

Buffer systems are conventional buffers and/or polymeric buffers.

Suitable buffers are, for example, all salts formed from weak acids and strong bases or strong acids and weak bases, the salts being from identical acids or bases or mixtures of salts from different acids or bases.

The buffers used in the case of copolymers carrying free acid groups, for example copolymers having free phosphono, sulfo or carboxyl groups, comprise at least one buffer system. The buffer region of the buffer system is preferably from pH 1 to 7. Suitable buffers or buffer solutions having a buffer region in the acidic range from pH 1 to 7 are for example buffers such as the Walpole buffer (acetic acid/Na acetate, pH 3.6–5.6), Gomori aconitate buffer (aconitic acid/NaOH, pH 2.5–5.7), Kolthoff buffer (borax/succinate, pH 3.5–5.8), Sørensen citrate buffer (disodium citrate/HCl, pH 2.2–4.8), Sørensen glycine buffer I (glycine, NaCl/HCl, pH 1.2–3.6), Clark and Lub phthalate buffer I (potassium biphthalate/HCl, pH 2.2–3.8), Clark and Lub phthalate buffer II (potassium biphthalate/NaOH, pH 4.0–6.2), Smith and Smith piperazine buffer (piperacine [sic], HCl/NaOH, pH 4.8–7.0), Clark and Lub potassium chloride/HCl buffer (KCl/HCl, pH 1.0–2.2), Gomori tris maleate buffer (tris maleate/NaOH, pH 5.2–8.6) or Gomori succinate buffer (succinate/NaOH, pH 3.8–6.0). Likewise, suitable buffers are MES, ADA, PIPES or ACES, which are common buffers in biochemistry, or amino acid buffers. Preference is given to buffers which are advantageously prepared from weak acids and their salts, such as sodium acetate/acetic acid, sodium borate/boric acid, sodium phosphate/phosphoric acid, hydrogen carbonate/sodium carbonate, sodium hydroxide/citric acid, sodium hydroxide/tartaric acid. Suitable buffers are also buffers prepared from weak bases and their salts. Individual buffers or mixtures can be used for adjusting the pH of the dispersions. The buffers used in the case of copolymers carrying free base groups, for example copolymers having free N-alkyl, amino or imino groups, comprise at least one buffer system. The buffer region of the buffer system is preferably from pH 7 to 13. Suitable buffers or buffer solutions having a buffer region in the basic range from pH 7 to 13 are for example buffers such as Clark and Lub borate buffer (boric acid, KCl/NaOH, pH 7.8–10.0), Delory and King buffer (carbonate/bicarbonate, pH 9.2–10.7) or Sørensen glycine buffer II (glycine, NaCl/HCl, pH 8.4–13). Likewise, suitable buffers are cholamine chloride, BES, TES, HEPES, acetamidoglycine, glycinamide, Tris, Bicine, Tricine or glycylglycine, which are common buffers in biochemistry, or amino acid buffers.

Preferred are buffers which can advantageously be prepared from weak acids and their salts. Suitable buffers are also buffers prepared from weak bases and their salts. Single buffers or mixtures can be used for adjusting the pH of the dispersions.

If polymeric buffers or buffer solutions are used for neutralizing the free acid groups or the free base groups of the copolymer, these polymeric buffers can be prepared advantageously by adding a neutralizing agent to a polymer carrying free acid groups or free base groups. Suitable polymers are copolymers carrying free acid groups or free base groups prepared by free-radical polymerization of (meth)acrylic acid, its derivatives, maleic acid, fumaric acid, itaconic acid, crotonic acid, vinylsulfonic acid, vinylphosphonic acid, polyethyleneimine and/or their salts, their esters and, if appropriate, their anhydrides. Suitable anhydrides are, for example, acrylic anhydride, methacrylic anhydride or maleic anhydride. Suitable polymers for preparing polymeric buffers are also natural polymers having free acid or base groups, such as alginic acid or hyaluronic acid. The monomer composition of the dispersion in the added polymeric buffer solution may be identical or different. The polymeric buffer or the polymeric buffer solution is preferably prepared from a portion of the dispersion to be dried by adding a neutralization agent. When preparing the polymer solution, the neutralization of the monomer units may be carried out partially or completely. Advantageously, from 50 to 100% by weight of the buffer polymer monomers able to form salts are in the salt form. Preferably, from 70 to 95% by weight of the monomers are in the salt form. Particularly preferred is the complete neutralization. Depending on what kind of free groups the polymer is carrying, bases or acids are used for neutralizing. Suitable neutralizing agents are all physiologically acceptable bases or acids, such as sodium hydroxide, sodium acetate, sodium phosphate, sodium carbonate, citric acid, tartaric acid, phosphoric acid, acetic acid and/or formic acid. However, the abovementioned buffers or buffer solutions are also suitable.

Single acids, bases or buffers for neutralizing or their combinations can be used for preparing the polymeric buffer solution.

The starting dispersion can thus be converted into a dispersion which affords a redispersible powder after drying simply by adjusting to an acidic or basic pH by the addition of at least one buffer system. Suitable buffer systems are single buffers and/or polymeric buffers or mixtures of buffers and/or polymeric buffers.

Irrespective of the nature of the salt-forming group, the same buffer and/or polymeric buffer can be used in all instances. The addition of an additional acid or base is not required, although perfectly possible. It is also possible to redisperse the dispersion powders obtained by free-radical polymerization and dried without the addition of buffer by stirring into at least one buffer and/or at least one polymeric buffer.

For economic reasons, the solids content of the dispersion to be dried is normally above 25% by weight. However, when preparing the polymeric buffer solution from such a dispersion, it is advantageous to adjust initially to a solids content of less than 15% by weight and to admix a neutralizing agent thereafter.

The dilute polymeric buffer solution prepared in this way is subsequently combined with the dispersion to be dried.

The solids content of the combination of dispersion and buffer and/or polymeric buffer solution is from 1 to 50% by weight. Preferred are 5 to 40% by weight, particularly preferred are 20 to 35% by weight.

It is an advantage that the dispersions prepared using the buffer and/or polymeric buffer addition according to the invention can withstand pH-fluctuations during processing without the formation of coagulum. By adding the buffer, the opening-pH, ie. the pH at which a polymer starts to swell and then dissolve, can be varied within precise ranges. This is particularly advantageous if a controlled release of an active compound is desired and optimum bioavailability is to be obtained by these means.

In principle, all copolymers obtainable by free-radical polymerization are suitable for preparing the redispersible polymer powders according to the invention.

Suitable monomer building blocks of these copolymers include monoethylenically unsaturated $C_3$–$C_8$-mono- and dicarboxylic acids, their anhydrides, esters, amides or salts, or mixtures of the carboxylic acids, anhydrides, esters, amides and salts mentioned.

Suitable carboxylic acids are, for example, acrylic acid, methacrylic acid, maleic acid, fumaric acid, itaconic acid or crotonic acid. Suitable anhydrides are, for example, acrylic anhydride, methacrylic anhydride or maleic anhydride.

Suitable esters are, for example, the $C_1$–$C_{10}$-alkyl esters or $C_1$–$C_{10}$-hydroxyalkyl esters of the abovementioned carboxylic acids. Preferred alkyl esters are the methyl, ethyl, propyl, butyl, i-butyl, tert-butyl, pentyl, i-pentyl-2,2-dimethylpropyl [sic], hexyl, i-hexyl, heptyl, i-heptyl, octyl, i-octyl-, 2-ethylhexyl, nonyl, i-nonyl, decyl or i-decyl esters of acrylic and/or methacrylic acid. Particularly preferred are the methyl, ethyl, propyl, butyl, i-butyl or tert-butyl esters.

If the monomers are used for polymerization in the form of their salts, alkaline earth metal, alkali metal or ammonium salts or the salts of organic amines are preferred; particularly preferred are alkali metal and ammonium salts.

Suitable basic monomer building blocks of the copolymers are vinylimidazole, vinylimidazoline, vinylimidazolidine, vinylpyridine, monoalkyl- or dialkylaminoalkyl esters or monoalkyl- or dialkylaminoalkylamides of the abovementioned unsaturated carboxylic esters.

Single monomers or mixtures can be used as starting monomers for preparing the copolymers.

Suitable for the redispersible dispersion powders according to the invention are advantageously copolymers comprising from 80 to 15% by weight, preferably from 70 to 30% by weight, of a free-radically polymerizable monomer capable of forming salts.

The dispersion powders preferably comprise from 20 to 85% by weight of units [sic], preferably from 30 to 70% by weight, of another monomer component consisting of at least one of the abovementioned alkyl esters of acrylic and/or methacrylic acid.

Suitable polymers are advantageously copolymers of methacrylic acid and ethyl acrylate, methacrylic acid and methacrylic esters, terpolymers of dimethylaminomethyl methacrylate, methyl and butyl methacrylate and copolymers of vinyl acetate and crotonic acid. Preferred copolymers are copolymers of methacrylic acid and ethyl acrylate.

Moreover, the polymer solution or dispersion can comprise other auxiliaries.

Auxiliaries include polysaccharides such as celluloses, for example hydroxyalkylcellulose [sic] such as methylcellulose or ethylcellulose, or hydroxy(alkyl)alkylcelluloses such as hydroxypropylcellulose or hydroxypropylmethylcellulose phthalate, starch, degraded starch, pectin, chitin, chitosan, arabinogalactan, xylan, gum xanthan, galactomannans such as gum ghatti, locust bean gum or gum tragacanth.

Proteins such as casein or gelatin or shellac can also be used as auxiliaries.

Also suitable are sugars, such as mono-, di- and trisaccharides, for example glucose, mannose or sucrose, sugar derivatives, sugar alcohols or urea. Auxiliaries also include substances such as pentaerythritol, pentaerythritol tetraacetate, polymers, such as polyethylene oxides or polypropylene oxides and their block copolymers, phosphatides, such as lecithin and lysolecithin, homo- and copolymers of vinylpyrrolidone, surfactants, citric acid, succinic acid, bile acids, sterols and other materials as described by J. L. Ford (Pharm. Acta Helv. 61, 69–88, 1986).

Surfactants are, for example, the various types of Brij® i.e. cetyl, lauryl, oleyl or stearyl ethers having from 2 to 100 polyoxyethylene units, the various types of Myrj® stearyl esters having from 8 to 100 polyoxyethylene units (=POE), the various types of Span® such as Span 20 (sorbitan monolaurates [sic]), Span 40 (sorbitan monopalmitates [sic]), Span 60 (sorbitan monostearates [sic]) or Span 80 (sorbitan monooleates [sic]), the various types of Tween® such as Tween 20 (POE (20) sorbitan monolaurate), Tween 40 (POE (20) sorbitan monopalmitates [sic]), Tween 60 (POE (20) sorbitan monostearates [sic]) or Tween 80 (POE (20) sorbitan monoleates [sic]), the various types of Triton® (octylphenol ethoxylates) such as Triton X-15, X-35, X-100 CG, X-305 (70%), X-405 (70%), X-705 (70%), ethoxylated castor oils such as polyoxyethylene glycerol triricinoleate 35 (Cremophor® EL) or polyoxyethylene glycerol trihydroxystearate 40 (Cremophor® RH40), ethoxylated 12-hydroxystearic acid such as polyoxyethylene-660–12'-hydroxystearate (Solutol® HS15) or sodium lauryl sulfate.

Auxiliaries further include, for example, fillers, smoothers, polishers, wetting agents, lubricants, mold parting agents, plasticizers, blowing agents, stabilizers, emulsifiers, colorants, flavors, plug-in agents [sic], flow agents and their mixtures.

Examples of plasticizers are low-molecular weight poly (alkylene oxides), such as poly(ethylene glycols), poly (propylene glycols), poly(ethylene propylene glycols), low-molecular weight organic plasticizers, such as glycerol, pentaerythritol, glycerol monoacetate, diacetate or triacetate, propylene glycol or sodium diethylsulfosuccinate, phthalates, citrates, sebacates or acetylated fatty acid glycerides.

Examples of colorants are known azo dyes, organic or inorganic pigments or colorants of natural origin. Preference is given to inorganic pigments.

Additionally other additives can be added, such as animal or vegetable fats, preferably in their hydrogenated form, in particular those that are solid at room temperature (20° C.). These fats are preferably of a melting point of 50° C. or higher. Preference is given to triglycerides of the $C_{12}$-, $C_{14}$-, $C_{16}$- and $C_{18}$-fatty acids. The same function can also be performed by waxes, such as carnauba wax, candelilla wax, ouricurri [sic] wax, sugar cane wax, retamo wax, animal waxes, such as beeswax, shellac waxes, Chinese insect waxes or lanolins, petroleum, lignite, peat and other montan waxes, polyolefin waxes, paraffin waxes, acid waxes, ester waxes, alcohol or amide waxes. These waxes can be unmodified or modified, partially or fully synthetic. Of course, single wax components such as wax acids, wax alcohols, wax ketones, wax hydroxyacids, paraffins, resin acids, polyterpenes, resin alcohols, sterols, petroleum jelly or fatty acids or mixtures can also be added.

These fats, waxes, fat or wax derivatives can be mixed in advantageously on their own or together with mono- and/or diglycerides or phosphatides, especially lecithin. The mono- and diglycerides are preferably derived from the abovementioned types of fats, ie. $C_{12}$-, $C_{14}$-, $C_{16}$- and $C_{18}$-fatty acids.

Further suitable auxiliaries are various emulsifiers. Commercially available emulsifiers are listed for example in M. and I. Ash, Handbook of Industrial Surfactants, Gower Publishing Co., Hants, (1993). They can be low-molecular weight or polymeric compounds. Low-molecular weight compounds generally contain a straight-chain or branched, saturated or unsaturated or unsaturated [sic], cyclic or acyclic, aromatic or aliphatic alkyl radical having from 8 to 40, preferably from 10 to 30, in particular from 12 to 22 carbon atoms in the molecule.

Moreover, stabilizers such as antioxidants, photostabilizers, hydroperoxide decomposers, radical scavengers and stabilizers to prevent microbial attacks may be added.

Auxiliaries are also bases and acids added to control the solubility of an active compound (cf. for example K. Thoma et al., Pharm. Ind. 51, 98–101 (1989)).

The auxiliaries can be added to the dispersion before or after drying.

If appropriate, the auxiliaries are added to the dispersion in an amount of from 0.5 to 50% by weight, preferably from 1 to 30% by weight, based on the total solids content of the dispersion.

Polymers containing free acids or bases are prepared in a conventional manner by free-radical polymerization by any of the known processes.

The copolymers employed advantageously for preparing the redispersible polymer powders can be prepared by various processes, for example by precipitation polymerization, inverse emulsion polymerization, inverse suspension polymerization, emulsion polymerization, suspension polymerization or solution polymerization.

The polymerization may be carried out batchwise or continuously, with or without the use of seed polymers, by initially charging all or some of the components of the reaction mixture, or by first partially charging and then making-up all or some of the components of the reaction mixture, or by metering in the components without initial charge.

DE-A-4 325 158, for example, discloses a process for precipitation polymerization.

For drying the ready-prepared dispersion, any of the customary techniques may be employed, such as thin film drying, fluidized-bed spray drying, spray drying or lyophilization.

In addition, the dispersions to be atomized can contain auxiliaries for spraying, such as polyvinyl alcohols, cellulose derivatives, starch derivatives, ligninsulfonates, polyacrylic acid and polyacrylamides. Suitable antiblocking agents which may be added are aluminum silicates, such as bentonites, kieselguhr, colloidal silica gel, diatomaceous earth, calcium carbonate, magnesium silicates such as talc or tricalcium phosphate.

The atomizing is preferably carried out as hydrodynamic atomizing by liquid pressure or air pressure through nozzles such as single component nozzles, multicomponent nozzles or disk nozzles using conventional atomizing equipment.

The basic principle is the atomization of the solution into very small droplets. These droplets have a very large surface area allowing fast evaporation. The small droplet diameter required is achieved by the speed of the atomizer wheel or the pressure of the atomizer gas. The degree of evaporation obtainable is sufficient to remove completely the moisture from the droplets Owing to the heat of evaporation lost and the short length of time the particles remain suspended, thermal damage to the product is avoided.

The liquid droplets can be dried in a conventional spray tower by using air or an inert gas such as nitrogen, argon or helium as drying gas which is passed through the drying tower in a cocurrent or countercurrent flow with the liquid droplets. The drying gas is preferably used in a cocurrent flow, the temperature of the gas when entering the tower being from 60 to 160, preferably from 90 to 140° C., and the temperature when leaving the tower being from 40 to 100, preferably from 60 to 80° C. The evaporation of the solvent can be carried out at atmospheric pressure or at from 0.6 to 1.2 bar.

The resulting powder can be separated off from the gas stream in a customary manner by using a cyclone.

The residual solvent content of the powder formed this way is generally not above 7.5% by weight. The particle size of the resulting powder particles is generally from 10 to 150 $\mu$m. Employing spray granulation, particles sizes of up to 450 $\mu$m can be achieved.

The polymer powders according to the invention redispersible in aqueous solution are far more readily redispersed than the prior art. In all experiments, redispersion was >90%. It is an advantage that films prepared from the dispersions according to the invention dissolve more quickly than films prepared from starting dispersions. Therefore, in the small intestine, the active compound is released more quickly from coated administration forms.

The redispersible dispersion powders according to the invention or the dispersions prepared therefrom or other secondary products are suitable for all solid or semisolid cosmetic or pharmaceutical formulations or for compositions used in crop or animal protection.

Solid or semisolid cosmetic or pharmaceutical formulations include, in a nonlimiting manner, tablets, crystals comprising an active compound, microtablets, sugar-coated tablets, pellets, pastilles, capsules, microcapsules and granules.

A particular method of application of the redispersible dispersion powders is the preparation of transdermal therapeutic systems.

Applications in crop protection include pheromone traps for harmful insects requiring a targeted, sustained release of the pheromone.

EXAMPLES

Example 1

Buffers used in Examples 1, 2, 5 and 6

Merck buffer pH 5.0 contains in 1 l 20.256 g of citric acid 7.84 g of NaOH

Merck buffer pH 6.0 contains in 1 l 12.526 g of citric acid 6.32 g of NaOH

Merck buffer pH 4.66 contains in 1 l 6.005 g of acetic acid 8.204 g of Na acetate 600 g of a 30% strength dispersion of Eudragit® L30D are admixed with 100 g of a 0.9% strength citric acid buffer with stirring. The resulting pH is then 4.0. The entire solution is then spray-dried by known methods (drying gas: cocurrent nitrogen, inlet temperature: 125° C., outlet temperature: 50° C.). A redispersible polymer powder is obtained which can be redispersed by stirring into water. The percentage of coagulum of <50 $\mu$m is 0% (determination see Example 7 [sic]). The opening-pH is 5.5.

Example 2

180 g of a methacrylic acid/ethyl acrylate copolymer (ratio 1:1) are stirred into an aqueous solution containing a 0.8% strength citrate buffer. This gives a dispersion of the methacrylic acid copolymer which was previously not redispersible.

Example 3

Preparation of a redispersible powder made of Eudragit® L30D (Röhm GmbH, acrylate dispersion made of ethyl acrylate and methacrylic acid)

a) Preparation of an Aqueous Polyacrylate Buffer Solution 93.4 g of a 10% strength dispersion (Eudragit® L30D) is converted into 114.1 g of an aqueous acrylate solution having a pH of 7.0 by the addition of 20.7 g of an aqueous 10% strength NaOH solution.

b) Preparation of the Mixture 1000 g of a 30% strength dispersion (Eudragit® L30D, pH about 2–3) are admixed with 114 g of the solution prepared under a). This gives a polyacrylate dispersion having a pH of 5.2. The dispersion is then spray-dried. This yields a redispersible powder.

Example 4 a) Preparation of an Aqueous Polyacrylate Buffer Solution 93.4 g of a 10% strength dispersion (Kollicoat® MAE 30D, BASF AG, acrylate dispersion made of ethyl acrylate and methacrylic acid, solids content about 30%) is converted into 114.1 g of an aqueous acrylate solution having a pH of 7.0 by the addition of 20.7 g of an aqueous 10% strength NaOH solution.

b) Preparation of the mixture 1000 g of a 30% strength dispersion (Kollicoat® MAE 30D, BASF AG, acrylate dispersion made of ethyl acrylate and methacrylic acid, solids content about 30%, pH about 2–3) are admixed with 114 g of the solution prepared under a). This gives a polyacrylate dispersion having a pH of 5.2. The dispersion is then spray-dried. This yields a redispersible powder.

Example 5

Coating for Tablets

In a horizontal drum coater (type Accela Cota, Manesty), 5000 g of propanolol [sic] tablets having an active compound content of 40 mg and a tablet weight of 250 mg were coated with a gastric juice-resistant film coating based on a redispersible methacrylic acid/ethyl acrylate copolymer comprising 2% of acetate buffer pH 4.66 based on the film former, thus applying 6 mg/cm² of gastric juice-resistant film former or 8 mg/cm² of solids.

The dispersion sprayed on was of the following composition:

| Pigment suspension: | |
|---|---|
| Titanium dioxide | 0.5% |
| Talc | 2.0% |
| Sicovit Red 30 | 0.5% |
| Kollidon 30 | 0.5% |
| Water | 10.0% |
| Coating suspension: | |
| Methacrylic acid/ethyl acrylate copolymer containing 2% of acetate buffer pH 4.66 | 15.0% |
| Triethyl citrate | 1.5% |
| Water | 70.0% |
| Total weight | 100.0% |

The pigment suspension was homogenized in a corundum disk mill. The methacrylic acid/ethyl acrylate copolymer containing 2% of acetate buffer was redispersed by slowly stirring the solids into water using a paddle stirrer, thus immediately forming a very fine dispersion.

1680.8 g of the spray suspension was sprayed on at an incoming air temperature of 46° C., an outgoing air temperature of 33° C. and a spray rate of 40 g/min. The coating was very smooth, even and a uniform red color.

The release in artificial gastric juice (pH: 1.2) showed the coating to be gastric juice-resistant for over 2 h, and the subsequent rebuffering to pH 6.8 demonstrated the rapid opening of the coating in the neutral region (99% release within 60 min).

Release rate:

| 60 min | pH 1.2 | 0.5% | of active compound released |
|---|---|---|---|
| 120 min | pH 1.2 | 0.8% | of active compound released |
| Rebuffering to 150 min | pH 6.8 | 99.0% | using phosphate buffer of active compound released |

Example 6

Redispersibility 20 g of redispersible methacrylic acid/ethyl acrylate copolymer comprising 2% of acetate buffer or 5% of citrate buffer based in each case on the film former were suspended in 80 g of demineralized water using a magnetic stirrer. The total stirring time was 60 min. The suspension was then passed through two sieves stacked on top of each other having mesh sites of 125 μm and 50 μm, and the residue—if present—was washed with a little water. After drying, the residue was determined gravimetrically.

| | Residue | |
|---|---|---|
| Result | 125 μm | 50 μm |
| Methacrylic acid/ethyl acrylate copolymer comprising 2% of acetate buffer pH 4.66 | 0.00% | 0.02% |
| Methacrylic acid/ethyl acrylate copolymer comprising 5% of citrate buffer pH 6.0 | 0.00% | 0.01% |

What is claimed is:

1. A process for preparing polymer powders redispersible in aqueous solution which comprises
   preparing a first dispersion of copolymers carrying free acid or base groups,
   adjusting the pH of said first dispersion by the addition of at least one buffer system to a pH of from 2.0 to 6.5, in the case of copolymers carrying acid groups, or to a pH of 7.5 to 12, in the case of copolymers carrying base groups,
   whereby some of the free acid or base groups are converted to salts thereof forming a second dispersion,
   and drying said second dispersion to obtain said polymer powders redispersible in aqueous solution,
   optionally, with the addition of auxiliaries prior to or after drying said second dispersion.

2. A process as claimed in claim 1, wherein the pH of the dispersion is adjusted by the addition of at least one buffer system to a pH of from 3.0 to 6.0 in the case of copolymers carrying acid groups or to from 7.5 to 11 in the case of copolymers carrying base groups prior to drying.

3. A process as claimed in claim 1, wherein the buffer system used comprises salts of weak acids and strong bases or salts of strong acids and weak bases.

4. A process as claimed in claim 1, wherein the buffer system used comprises polymeric buffers obtainable by adding a neutralizing agent to a polymer carrying free acid or base groups.

5. A process as claimed in claim 1, wherein the polymer powder used comprises copolymers carrying free carboxyl or amino groups.

6. A process as claimed in claim 1, wherein the polymer powder used comprises copolymers having from 20 to 85% by weight of an alkyl ester of acrylic and/or methacrylic acid and from 80 to 15% by weight of a free-radically polymerizable monomer capable of forming salts.

* * * * *